US 8,480,686 B2
Jul. 9, 2013

(12) United States Patent
Bakos et al.

(54) METHODS AND DEVICES FOR DELIVERING AND APPLYING SUTURE ANCHORS

(75) Inventors: Gregory J. Bakos, Mason, OH (US);
William D. Fox, New Richmond, OH (US); Duane Linenkugel, Cincinnati, OH (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 899 days.

(21) Appl. No.: 12/237,877

(22) Filed: Sep. 25, 2008

(65) Prior Publication Data

US 2010/0076462 A1    Mar. 25, 2010

(51) Int. Cl.
*A61B 17/10* (2006.01)

(52) U.S. Cl.
USPC ............ 606/139; 606/146; 606/151; 606/232

(58) Field of Classification Search
USPC ............... 606/139, 142, 143, 146, 148, 213, 606/232, 144, 145, 147, 151
See application file for complete search history.

(56) References Cited

U.S. PATENT DOCUMENTS

| | | | |
|---|---|---|---|
| 5,100,415 A | 3/1992 | Hayhurst | |
| 5,268,001 A * | 12/1993 | Nicholson et al. | 606/232 |
| 5,391,182 A | 2/1995 | Chin | |
| 5,507,757 A | 4/1996 | Sauer et al. | |
| 5,573,540 A * | 11/1996 | Yoon | 606/139 |
| 5,810,845 A | 9/1998 | Yoon | |
| 6,117,144 A | 9/2000 | Nobles et al. | |
| 6,290,674 B1 | 9/2001 | Roue et al. | |
| 6,315,784 B1 | 11/2001 | Djurovic | |
| 6,447,524 B1 | 9/2002 | Knodel et al. | |
| 6,524,316 B1 | 2/2003 | Nicholson et al. | |
| 6,626,930 B1 | 9/2003 | Allen et al. | |
| 6,699,263 B2 * | 3/2004 | Cope | 606/232 |
| 6,896,685 B1 | 5/2005 | Davenport | |
| 6,911,034 B2 | 6/2005 | Nobles et al. | |
| 7,722,629 B2 | 5/2010 | Chambers | |

(Continued)

FOREIGN PATENT DOCUMENTS

| | | |
|---|---|---|
| EP | 1808134 A2 | 7/2007 |
| EP | 1938760 A1 | 7/2008 |

(Continued)

OTHER PUBLICATIONS

International Search Report, Application No. PCT/US2009/057408, mailed Dec. 16, 2009.

(Continued)

*Primary Examiner* — Corrine M McDermott
*Assistant Examiner* — Alexander Orkin
(74) *Attorney, Agent, or Firm* — Nutter McClennen & Fish LLP

(57) ABSTRACT

Methods and devices are provided for deploying and applying a suture anchor. In one embodiment, a surgical device is provided having a shaft configured to be introduced into a body and to deliver a suture anchor with a coil of suture attached thereto to tissue. The shaft can be configured to deploy the suture anchor through tissue and to deliver the coil of suture into a body cavity such that the suture extending from the coil extends through the tissue to allow the anchor to engage the tissue. The coil can remain in the body cavity for subsequent use.

22 Claims, 7 Drawing Sheets

U.S. PATENT DOCUMENTS

| | | | |
|---|---|---|---|
| 7,744,613 B2 | 6/2010 | Ewers et al. | |
| 7,824,382 B2 | 11/2010 | Reihl et al. | |
| 7,887,551 B2 | 2/2011 | Bojarski et al. | |
| 2002/0049453 A1 | 4/2002 | Nobles et al. | |
| 2003/0009177 A1 | 1/2003 | Middleman et al. | |
| 2003/0195562 A1* | 10/2003 | Collier et al. | 606/232 |
| 2003/0204195 A1* | 10/2003 | Keane et al. | 606/146 |
| 2004/0162568 A1* | 8/2004 | Saadat et al. | 606/139 |
| 2004/0186486 A1 | 9/2004 | Roue et al. | |
| 2004/0230095 A1 | 11/2004 | Stefanchik et al. | |
| 2005/0113851 A1 | 5/2005 | Swain et al. | |
| 2005/0251205 A1* | 11/2005 | Ewers et al. | 606/232 |
| 2005/0267533 A1* | 12/2005 | Gertner | 606/232 |
| 2006/0025819 A1* | 2/2006 | Nobis et al. | 606/232 |
| 2006/0030885 A1 | 2/2006 | Hyde | |
| 2006/0142784 A1 | 6/2006 | Kontos | |
| 2007/0005080 A1 | 1/2007 | Wolniewicz et al. | |
| 2007/0032823 A1 | 2/2007 | Tegg | |
| 2007/0073342 A1* | 3/2007 | Stone et al. | 606/232 |
| 2007/0100348 A1 | 5/2007 | Cauthen et al. | |
| 2007/0100354 A1 | 5/2007 | Cauthen, III et al. | |
| 2007/0112384 A1 | 5/2007 | Conlon et al. | |
| 2007/0112385 A1 | 5/2007 | Conlon | |
| 2007/0260273 A1 | 11/2007 | Cropper et al. | |
| 2007/0270889 A1 | 11/2007 | Conlon et al. | |
| 2008/0086172 A1 | 4/2008 | Martin et al. | |
| 2008/0097483 A1* | 4/2008 | Ortiz et al. | 606/148 |
| 2008/0103527 A1 | 5/2008 | Martin et al. | |
| 2008/0161850 A1 | 7/2008 | Weisenburgh et al. | |
| 2008/0275474 A1 | 11/2008 | Martin et al. | |
| 2010/0076488 A1 | 3/2010 | Spivey et al. | |
| 2010/0106166 A1 | 4/2010 | Cropper et al. | |

FOREIGN PATENT DOCUMENTS

| | | |
|---|---|---|
| FR | 2785171 A1 | 5/2000 |
| WO | WO-0222026 A1 | 3/2002 |
| WO | WO-2008137534 | 11/2008 |
| WO | WO-2008137537 | 11/2008 |

OTHER PUBLICATIONS

International Search Report, Application PCT/US2009/061616, mailed Mar. 5, 2010, 8 pages.
International Search Report, Application PCT/US2009/057415, mailed Jan. 28, 2010, 8 pages.
Written Opinion for PCT/US2009/057408 dated Dec. 16, 2009 (7 pages).
Written Opinion for PCT/US2009/057415 dated Jan. 28, 2010 (7 pages).
Written Opinion for PCT/US2009/061616 dated Mar. 5, 2010 (7 pages).
International Preliminary Report on Patentability for PCT/US2009/057408 issued Mar. 29, 2011 (7 Pages).
International Preliminary Report on Patentability for PCT/US2009/057415 mailed Apr. 7, 2011 (8 Pages).
International Preliminary Report on Patentability for PCT/US2009/061616 issued May 3, 2011 (7 Pages).

* cited by examiner

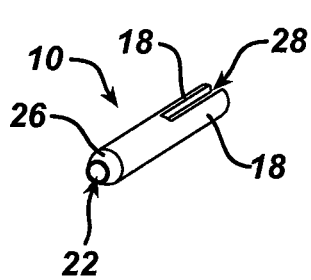
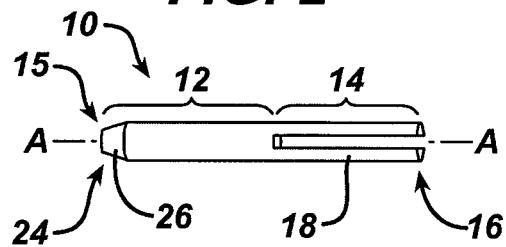
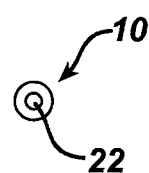
FIG. 1  FIG. 2  FIG. 3
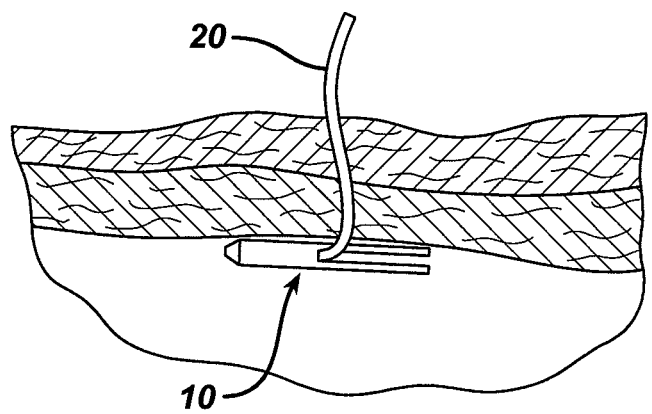
FIG. 4
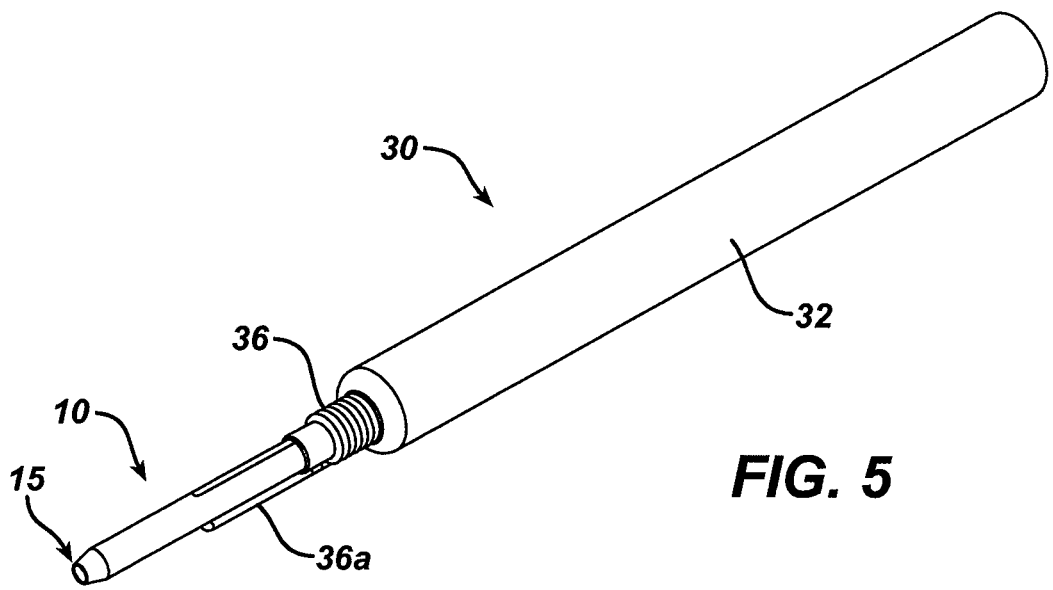
FIG. 5

FIG. 14
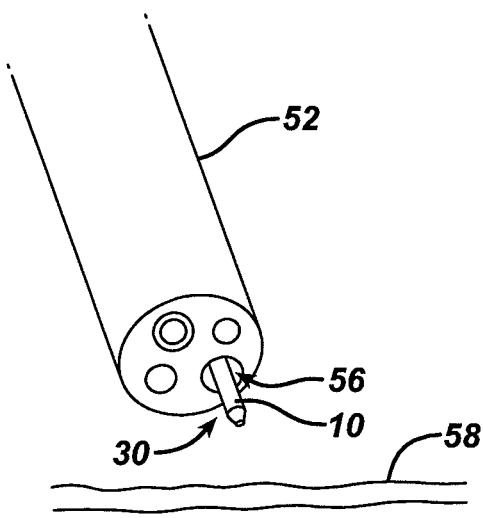
FIG. 15
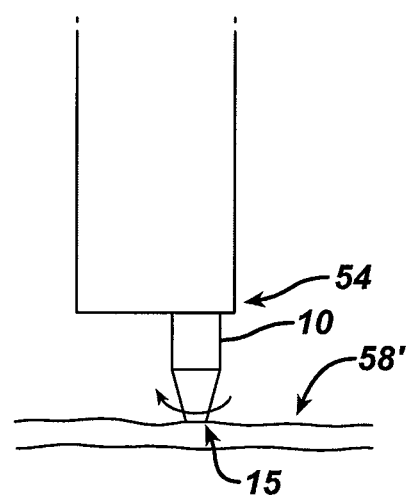
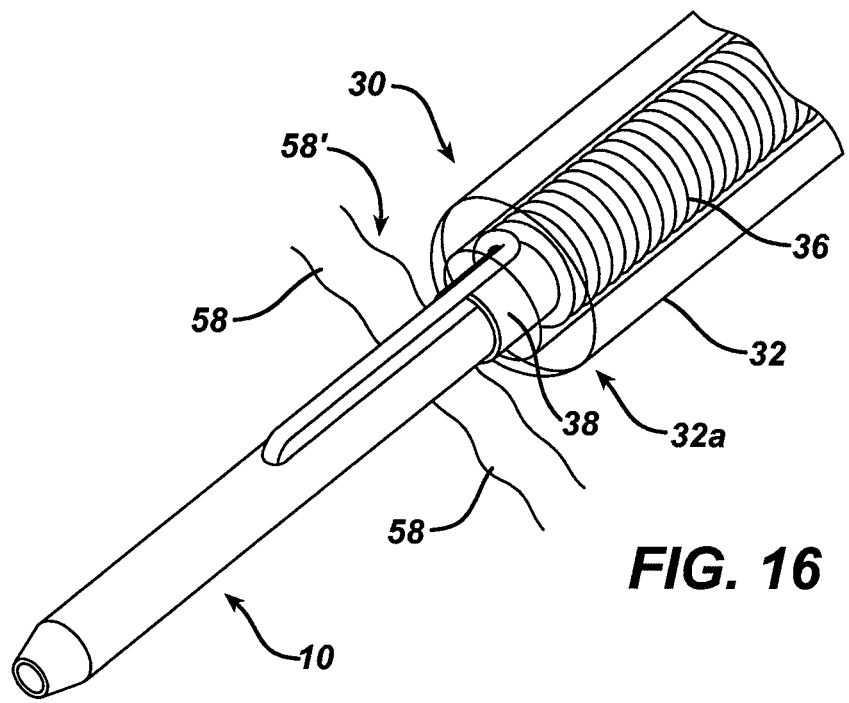
FIG. 16

METHODS AND DEVICES FOR DELIVERING AND APPLYING SUTURE ANCHORS

FIELD OF THE INVENTION

The present invention relates to suture anchors and associated devices and methods for endoscopically suturing tissue.

BACKGROUND OF THE INVENTION

Endoscopic surgery, including procedures performed by way of endoscopic instruments such as gastroscopes, colonoscopes, laparoscopes, and the like, may be preferred as an alternative to open surgery due to the many advantages attributed to such "minimally invasive" techniques, such as shortened hospital stays, reduced recovery time, reduced risk of complications, and diminishment of the amount of and/or visibility of scarring caused by a surgical intervention. In many endoscopic procedures, as in open surgery, there are instances where a surgeon may desire to repair damaged or diseased tissues by apposing the tissues together using a suture. However, the suturing devices, stapling devices, and other fastener applicators that have been developed to aid surgeons performing open surgery generally cannot be easily redesigned to be passed through a flexible endoscopic instrument, which may have a working channel having an internal diameter in the range of about 2.0 to 4.0 millimeters.

To address these problems, various suture anchors and applicator devices have been developed to permit surgeons to endoscopically emplace sutures within tissues. Such suture anchors may be deployed using applicator devices that are inserted within and extended through the working channel of an endoscope, carrying a suture anchor to the site of repair. The suture anchor typically has suture attached thereto. The length of suture required to extend through the applicator device and into the body can be long, and the suture can get knotted or tangled en route to and/or in the body, thereby prolonging the surgical procedure while the suture is repaired or replaced. The applicators typically include a cannulated needle portion which permits the surgeon to penetrate the tissues adjacent to diseased or damaged tissue and to deploy the suture anchor into the tissue to be apposed in a repair. Such needle penetration presents the risk that nearby organs may be accidentally injured by the needle of the applicator. A physician normally cannot see anatomical structures on the distal side of the tissue layers when the needle is being pushed through the tissue layers. Therefore, there is a risk that adjacent organs may be accidentally injured by the penetrating needle.

Accordingly, there remains a need for methods and devices for deploying suture anchors with improved suture management and decreased chances of damaging adjacent tissue.

SUMMARY OF THE INVENTION

The present invention generally provides methods and devices for delivering and applying a suture anchor. In one embodiment, a suture anchor deployment apparatus is provided that includes a suture anchor configured to engage tissue, a shaft having a distal end configured to deploy the suture anchor, and a suture spool releasably disposed around the shaft and having a coil of suture disposed thereon and coupled to the suture anchor.

The apparatus can have any number of variations. For example, the suture anchor can be coupled to a distal end of the shaft. In some embodiments, the shaft can be configured to be retracted into the distal end of the suture spool to release the suture anchor. The shaft can also be configured to rotate the suture anchor to cause the suture anchor to penetrate through tissue. In some embodiments, the suture anchor can include a circular cutting tip. For yet another example, the suture anchor can have a tapered distal end. For still another example, the coil of suture can have an uncoiled length that is at least about ten times a coiled length of the coil of suture. In some embodiments, the apparatus can include a sheath disposed around the suture spool. The sheath can be flexible such that the sheath can be passed through a tortuous pathway.

In some embodiments, the apparatus can also include a spool retaining member releasably coupled to a proximal end of the suture spool. The shaft can be disposed through the spool retaining member, and it can be effective to maintain the suture spool and the spool retaining member in mated engagement. Rotating the spool retaining member, with the shaft removed from the suture spool, can be effective to release the suture spool from mated engagement with the spool retaining member.

In another embodiment, a suture anchor deployment apparatus is provided that includes a suture spool having a suture wound therearound, a suture anchor disposed adjacent to a distal end of the suture spool and coupled to the suture, and a shaft disposed through the suture spool and configured to advance the suture anchor through tissue. The apparatus can have any number of variations. For example, the apparatus can include a spool retaining member releasably coupled to a proximal end of the suture spool and disposed around the shaft. Rotating the spool retaining member, with the shaft removed from the suture spool, can be effective to release the suture spool from mated engagement with the spool retaining member. The shaft can be configured to rotate the suture anchor to cause the suture anchor to penetrate through tissue. The suture anchor can have a beveled edge at its distal end configured to cut tissue.

In other aspects, a method for deploying a suture anchor is provided that includes advancing a shaft to advance a suture anchor positioned distal of a distal end of a suture spool disposed around the shaft through tissue such that the suture anchor engages the tissue and a suture coupled to the suture anchor extends through the tissue and is wound around the suture spool. The method can have any number of variations. For example, the method can include rotating the shaft as it is advanced to cause a cutting tip on the suture anchor to cut through tissue. For another example, the method can include removing the shaft from the suture spool to release the suture spool. The suture spool can be grasped with a grasper, and the grasper can be manipulated to unwind at least a portion of the suture from the suture spool. For yet another example, the method can include, prior to advancing the suture anchor, advancing the shaft through a working channel of an endoscope. As still another example, the method can include deploying at least one additional suture anchor through the tissue, each of the at least one additional suture anchors having a suture coupled thereto that extends through the tissue, forming a puncture through the tissue, and manipulating the sutures attached to the suture anchor and the at least one additional suture anchor to close the puncture.

BRIEF DESCRIPTION OF THE DRAWINGS

The invention will be more fully understood from the following detailed description taken in conjunction with the accompanying drawings, in which:

FIG. 1 is a perspective view of one embodiment of a suture anchor;

FIG. 2 is a side view of the suture anchor of FIG. 1;

FIG. 3 is an end view of the suture anchor of FIG. 1;

FIG. 4 is a schematic partially cross-sectional view of the suture anchor of FIG. 1 deployed in a body;

FIG. 5 is a perspective view of one embodiment of a surgical device configured to deliver and apply a suture anchor;

FIG. 14 is a side partially cross-sectional view of the device of FIG. 5 advanced through the endoscope of FIG. 13 and positioned adjacent to tissue;

FIG. 15 is side partially cross-sectional view of the suture anchor being rotated in the device of FIG. 14 to penetrate through the tissue;

FIG. 16 is perspective partially cross-sectional transparent view of the device advanced through the tissue of FIG. 15;

DETAILED DESCRIPTION OF THE INVENTION

Figure 6:
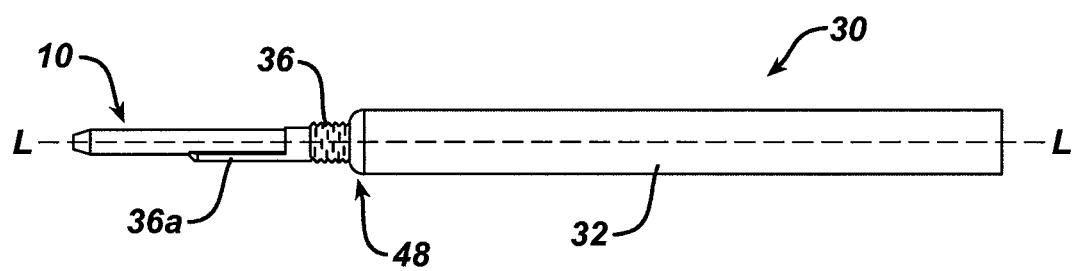
FIG. 6 is a side view of the device of FIG. 5.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for deploying and applying a suture anchor. In one embodiment, a surgical device is provided having a shaft configured to be introduced into a body, e.g., through a scoping device, and to deliver a suture anchor with a coil of suture attached thereto to tissue. The shaft can be configured to deploy the suture anchor through tissue and to deliver the coil of suture into a body cavity such that the suture extending from the coil extends through the tissue to allow the anchor to engage the tissue. The coil can remain in the body cavity for subsequent use. Such a configuration is particularly advantageous as the coil of suture facilitates suture management, e.g., by preventing entanglement of the suture with itself or with other sutures attached to other suture anchors. Delivering a suture anchor with a coil of suture attached thereto is also advantageous as it can allow one or more anchors to be pre-deployed in tissue prior to forming a puncture through the tissue. Once a puncture is formed, unless tension is applied to the tissue, it can be difficult to insert a suture anchor through tissue adjacent to the puncture for closing the puncture. Thus, deployment of the anchor(s) prior to puncture formation can be more easily achieved, and the coil of suture retains the suture until needed, e.g., for subsequently closing the puncture.

A person skilled in the art will appreciate that the term "tissue" as used herein is intended to encompass a variety of materials, e.g., organs, blood vessels, body lumens, and any other material that needs to be secured in a surgical procedure. A person skilled in the art will also appreciate that while the methods and devices are described in connection with endoscopic procedures in which the suture anchor is delivered through a natural orifice, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. A person skilled in the art will also appreciate that the methods and devices disclosed herein can be used with any surgical tool, such as a scoping device, having a cannula or other working channel through which the shaft of a surgical instrument can be advanced and that is configured to be inserted into a body, such as through a natural orifice, through a puncture hole formed in tissue, and in any other way appreciated by a person skilled in the art. Non-limiting examples of a scoping device include an endoscope, a laparoscope, and a colonoscope. While the scoping device can be rigid or flexible, in an exemplary embodiment, the scoping device is flexible. Furthermore, the scoping device can be configured to pass through any portion of a body, but in an exemplary embodiment, the scoping device is configured to pass through a tortuous pathway. A person skilled in the art will appreciate that the term "tortuous pathway" as used herein is intended to include a tubular body lumen or organ, e.g., the colon or esophagus. Devices disclosed herein can alternatively or additionally be introduced into a body through an auxiliary passageway along the outside of a scoping device. One non-limiting example of a surgical instrument that provides such an auxiliary passageway can be found in commonly-owned U.S. Patent Publication No. 2004/0230095, which is hereby incorporated by reference in its entirety.

The devices discussed herein can be made from any combination of rigid and/or flexible materials, but in an exemplary embodiment the materials are biocompatible. A person skilled in the art will appreciate that the term "flexible" as used herein is intended to encompass a variety of configurations. Generally, a "flexible" member has some degree of elasticity, e.g., is capable of bending without breaking. In an exemplary embodiment, the device or at least portions thereof are composed of at least one biocompatible and flexible material, e.g., plastic, titanium, stainless steel, etc. Various portions of the device can also be formed from a shape memory material, such as Nitinol.

A suture anchor coupled to and deployable from the shaft can include any suture anchor having a suture attached thereto in any way appreciated by a person skilled in the art. The suture anchor can be configured to secure tissue with its attached suture, as will also be appreciated by a person skilled in the art. Any size and shape of suture anchor can be used with the device. The suture anchor can be composed of any one or more materials as will be appreciated by a person skilled in the art, e.g., titanium, tantalum, stainless steel, a shape memory material, plastic, etc. In an exemplary embodiment, the suture anchor is composed of a rigid material such as stainless steel or titanium. The suture anchor can also have a fixed configuration, or an expandable suture anchor can be used. For example, the suture anchor can be constrainable to a first configuration for deployment into tissue (e.g., when disposed in a scoping device working channel and/or in a sheath as discussed below) and be expandable when unconstrained to a second configuration (e.g., when deployed from the shaft) for resisting pull-out from the tissue, such as when the suture anchor is composed of a shape memory material.

FIGS. 1-4 illustrate one exemplary embodiment of a suture anchor 10 that can be delivered and applied using the methods and devices described herein. FIGS. 1-3 are perspective views of the anchor 10, while FIG. 4 shows the anchor 10 following deployment into tissue and having a suture 20 attached thereto. The anchor 10 can have any shape, size, and configuration. The anchor 10 can have a uniform or non-uniform diameter along its longitudinal length and preferably has a maximum diameter that allows the anchor 10 to be coupled to a shaft and/or disposed within a sheath as discussed further below.

The illustrated anchor 10 generally includes an elongate body that is configured to be positioned along a tissue surface, and that includes a suture coupled preferably to a mid-portion thereof. Such a configuration allows the elongate body to be inserted through tissue along the elongate body's longitudinal axis and then to pivot, e.g., about 90 degrees, to rest against and engage the tissue surface, e.g., as shown in FIG. 4. The suture attached to the elongate body will extend through the tissue, thus allowing the suture to be used to reposition, tension, secure, or otherwise manipulate the tissue. While the elongate body can have various configurations, in an exemplary embodiment, the elongate body includes at least a portion that is configured to seat the suture to facilitate insertion of the suture anchor through tissue. In the illustrated embodiment, the elongate body has a cannulated portion 12 and a bifurcated portion 14. The cannulated portion 12 can extend along any partial length of the body and can, as illustrated, be substantially cylindrical along any or all portions of its length. The bifurcated portion 14 can also extend along any partial length of the body, although the cannulated and bifurcated portions 12, 14 preferably each have substantially the same length to allow the suture to extend from the anchor 10 at substantially a mid-portion thereof, e.g., at a junction of the cannulated and bifurcated portions 12, 14. The bifurcated portion 14 can form a pair of opposed legs 18. The legs 18 can have any size, shape, and configuration. As illustrated, the legs 18 of the bifurcated portion 14 include two substantially half-cylinders. The bifurcated portion 14 can include an angled portion (not shown) at distal portions of the legs 18 that splays away from a central longitudinal axis A of the anchor 10. The angled portion can help retain the anchor 10 inside the surgical device until deployment of the anchor 10 to tissue. The angled portion can have any length e.g., between approximately one eighth and one quarter of the overall length of the anchor 10.

The cannulated portion 12 can have a lumen 22 extending therethrough and in communication with an opening 28 between the opposed legs 18. In an exemplary embodiment, the lumen 22 can have at least a partially substantially circular cross-section to help prevent a suture disposed therein from snagging on or otherwise being impeded by the anchor 10. FIG. 3 is an end view of the anchor 10 showing a substantially circular cross-section of the anchor 10 with the lumen 22 (and the opening 28) extending therethrough between open terminal ends 24, 16 of the anchor 10. A person skilled in the art will appreciate that the cannulated portion 12 can be cannulated during manufacturing simply to facilitate formation of the legs 18 in the bifurcated portion 14. In other embodiments, one or both of the suture anchor's terminal ends can be closed, and/or the suture anchor or portions thereof can be a solid member, e.g., without a passageway extending fully or partially therethrough. A closed terminal end can help prevent tissue or other body matter from entering the anchor 10, e.g., if tissue collection or fluid flow through the anchor 10 is not desired. At least one of the anchor's terminal ends 24 can include a tapered nose 26, as illustrated. The nose 26 can have any length along the longitudinal axis A and have a truncated-cone shape at its distal-most end, although the nose 26 can have another tapered shape, e.g., a cone shape, or not be tapered at all. A tapered nose 26 can help the anchor 10 more easily pass through tissue.

At least one of the anchor's terminal ends 24, 16 can include a cutting tip 15 configured to cut tissue, as discussed further below. The cutting tip 15 is preferably formed on a distal-most end of the tapered nose 26, as illustrated. The cutting tip 15 can have any size, shape, and configuration, as will be appreciated by a person skilled in the art. As illustrated in this embodiment, the cutting tip 15 can be configured as a circular cutting tip, e.g., having a circular cross-section, at the terminal end 24 having a sharp edge around at least a portion of the terminal end's perimeter or circumference (and/or end surface if the terminal end is closed). As a non-limiting example of the cutting tip 15, the anchor's terminal end 24 can include a beveled edge (including a chamfered edge) around at least a portion of its perimeter, e.g., around its entire circumference, along equidistantly spaced portions around its circumference, etc. Further non-limiting examples of the cutting tip 15 include the anchor 10 having a pointed needle tip, an electronic cutter, etc.

Various other, non-limiting embodiments of a suture anchor are described in commonly owned U.S. Patent Publication No. 2007/0112384, U.S. Patent Publication No. 2007/0112385, U.S. Patent Publication No. 2008/0161850, and U.S. Pat. No. 6,447,524, all of which are hereby incorporated by reference in their entireties.

The suture 20 attached to the anchor 10 can be any conventional surgical suture, as will be appreciated by a person skilled in the art. The suture 20 can be composed of any material, e.g., cat gut, silk, polypropylene, polyester, stainless steel, etc., and the suture 20 can have any shape and size, e.g., 2/0 suture, 3/0 suture, 4/0 suture, etc. The suture can be attached to the suture anchor 10 in any way, and at any location of the anchor 10, e.g., within the inner lumen 22, on an outside surface of the anchor 10, etc., as will be appreciated by a person skilled in the art. For non-limiting example, suture can be crimped in a surface of the suture anchor 10, molded to the suture anchor 10, or knotted to the suture anchor 10. Non-limiting examples of various ways to attach a suture to a suture anchor are described in previously mentioned U.S. Patent Publication No. 2007/0112384 and U.S. Patent Publication No. 2008/0161850.

FIGS. 5-9 illustrate a surgical device 30 configured to deliver and apply a suture anchor, e.g., the suture anchor 10 shown in FIGS. 1-3, having a coil of suture 36 attached thereto, to a tissue at a surgical site in a body of a patient. In an exemplary embodiment, the device 30 can include an elongate shaft 34 that can be flexible to allow it to be introduced into a body of a patient usually a minimally invasive technique, such as through a working channel of a flexible scoping device (or through an auxiliary channel of a flexible scoping device) having at least its distal end disposed in a body. A person skilled in the art will appreciate that having a flexible shaft 34 indicates that at least a portion of the shaft 34 is composed of one or more flexible materials. The shaft 34 can be configured to have the anchor 10 removably coupled at a distal portion 34a thereof. The shaft 34 can also be configured to be movably disposed through a suture spool 38 having the coil of suture 36 disposed thereon. The shaft 24 can also be movably disposed through a spool retaining member 40 releasably coupled to the suture spool 38. The anchor 10 can be coupled to a distal portion 36a of the coil of suture 36, thereby allowing at least a portion of the coil of suture 36 to be deployed, e.g., unwound from the suture spool 38, at least when the anchor 10 is deployed from the shaft 34. The device 30 can also include an outer tube or cannulated sheath 32 in which the anchor 10, the shaft 34, the coil of suture 36, the suture spool 38, and the spool retaining member 40 can be disposed.

As discussed further below, the anchor 10 can be deployed from the shaft 34 by advancing the anchor 10 through tissue to a desired location in the body and retracting the shaft 34 relative to the anchor 10 to release the anchor 10, with the coil of suture 36 attached thereto, from the shaft 34. The coil of suture 36 can optionally be deployed from the device 30 by retracting the shaft 34 through the suture spool 38, which can release the suture spool 38 from mated engagement with the spool retaining member 40 to allow the suture spool 38, with the coil of suture 36 disposed thereon, to be released into the body. The coil of suture 36 can thus be available during and/or subsequent to a surgical procedure for suturing or otherwise manipulating tissue.

Figure 9:
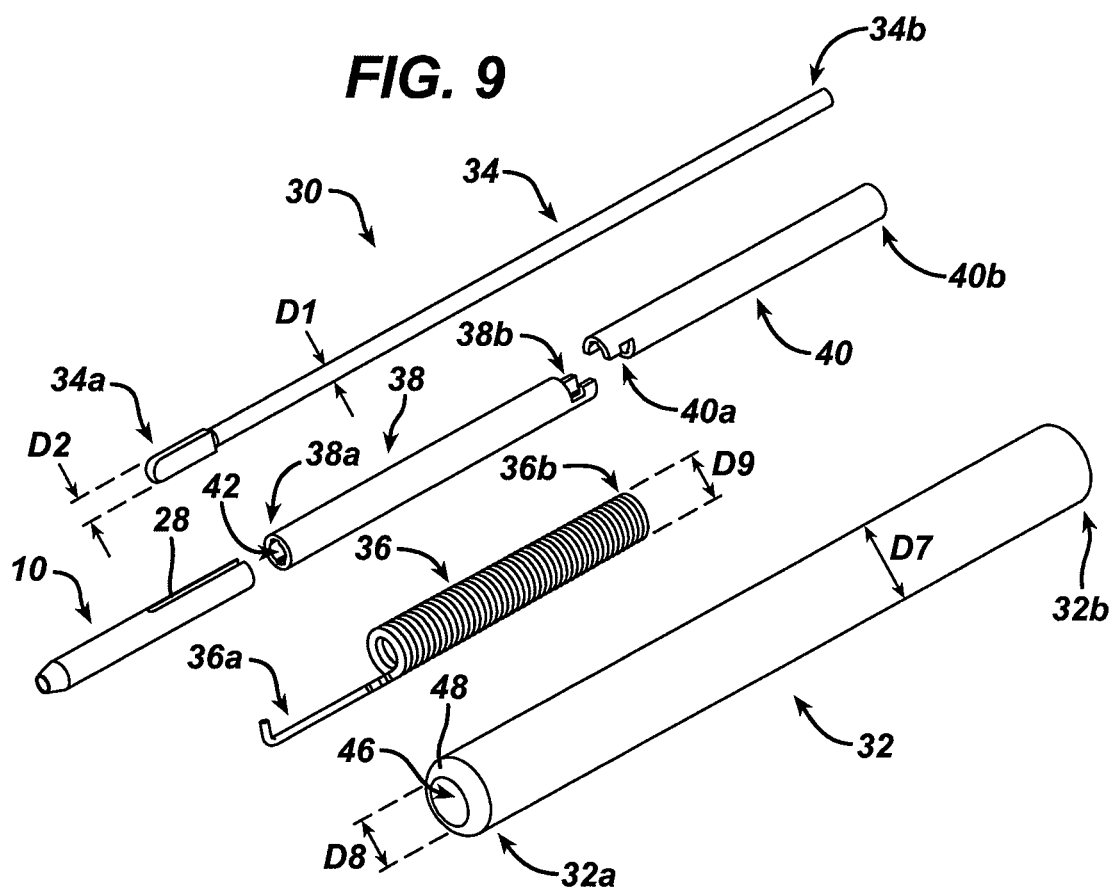
FIG. 9 is an exploded view of the device of FIG. 5.

The shaft 34, best seen in FIG. 9, can have a variety of sizes, shapes, and configurations. Generally, the shaft 34 can have a shape, size, and configuration that allows it to releasably engage the anchor 10 between the opposed legs 18 in the opening 28 (see FIG. 1) and to be movably disposed through pathways 42, 44, 46 in the suture spool 38, the spool retaining member 40, and the sheath 32, respectively. The shaft 34 can be rigid, flexible, or a combination thereof, but it is preferably flexible at least along a substantial length thereof. The shaft's distal portion can be less flexible or more rigid than the remainder of the shaft 34 to facilitate engagement and/or deployment of the anchor 10. The shaft 34 is preferably solid, but the shaft 34 can have one or more hollow portions. The shaft 34 is shown in this embodiment as a substantially cylindrical rod or wire (except in the distal portion 34a), which can help the shaft 34 pass smoothly into a body. The shaft 34 can, however, have any constant or varying shape along its longitudinal length, and the diameter can be uniform or non-uniform along its longitudinal length. In an exemplary embodiment, the shaft 34 has a substantially uniform diameter D1 along its longitudinal length except in its distal portion 34a, which has a larger maximum diameter D2 to help engage the anchor 10. The distal portion 34a can have a variety of sizes, shapes, and configurations, but as shown in the illustrated embodiment, the distal portion 34a can be a flattened portion or a substantially planar tab. The tab can have a variety of shapes, e.g., rounded rectangular (as shown), rectangular, elliptical, etc. The shape and size of the distal portion 34a can generally correspond to the shape and size of the opening 28 in the anchor 10. In an exemplary embodiment, the distal portion 34a is sized to form an interference or press fit within the opening 28 to engage the anchor 10.

Figure 8:
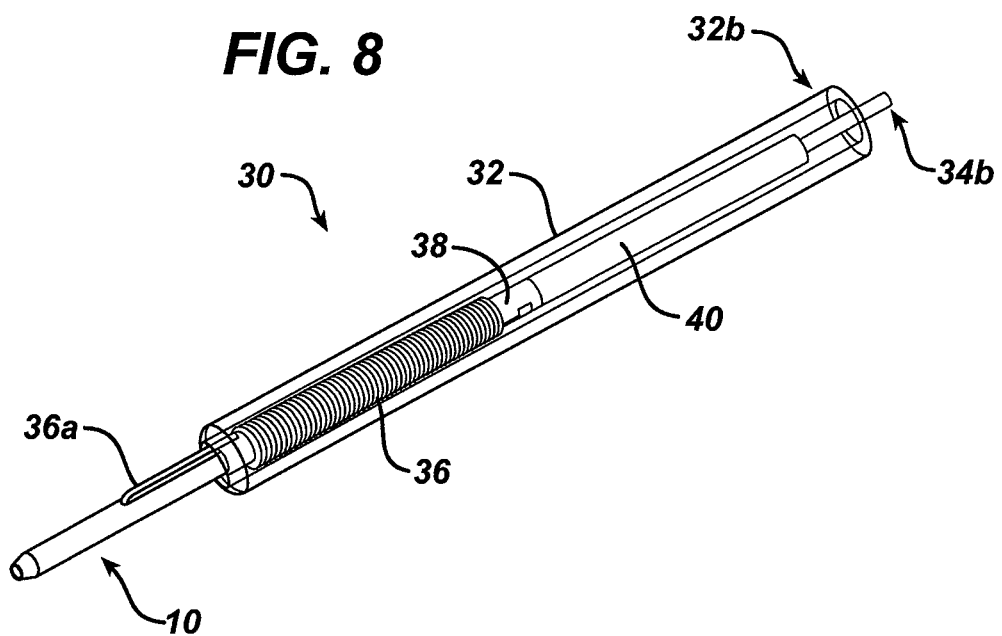
FIG. 8 is a partially transparent perspective view of the device of FIG. 5.

The shaft 34 can have any longitudinal length, but, as best seen in FIG. 8, its length is preferably long enough to allow the shaft's proximal portion 34b to extend beyond a proximal end 32b of the sheath 32 to allow the shaft 34 to be manipulated outside the body when the shaft's distal portion 34a is disposed in a body and/or in a scoping device.

As mentioned above, the shaft 34 can be movable, manually and/or electronically, relative to at least one other component of the device 30 and/or to a scoping device in which the shaft 34 is disposed. The shaft 34 can be movable in any one or more ways, but in an exemplary embodiment, the shaft 34 is slidably and rotatably movable relative to the sheath 32 within the sheath's pathway 46. The shaft 34 can be slidably movable along a central longitudinal axis L of the device 30 to allow the distal portion 34a of the shaft 34 to be selectively advanced beyond the sheath's distal end 32a to deploy the anchor 10. The shaft 34 can also be rotatably movable about the device's central axis L to rotate the anchor 10 to facilitate insertion through tissue. The shaft 34 can be moved in a variety of ways, although in an exemplary embodiment, the shaft 34 can include a handle and/or controls (not shown) at its proximal portion 34b to help manipulate the shaft 34, as will be appreciated by a person skilled in the art. Any type of handle and/or controls having any configuration can be used. For non-limiting example, the shaft's proximal portion 34b can include a knob to help guide the device 24 into a body, slidably and/or rotationally move the shaft 34 within and relative to the sheath 32, deploy the anchor 10, and/or perform any other functions as will be appreciated by a person skilled in the art. The device 30 can include a locking mechanism, e.g., a catch, a switch, etc., to lock the shaft 34 in a desired position when the distal portion 34a is contained within and/or extends beyond the sheath's distal end 32a, as will be appreciated by a person skilled in the art.

Figure 7:
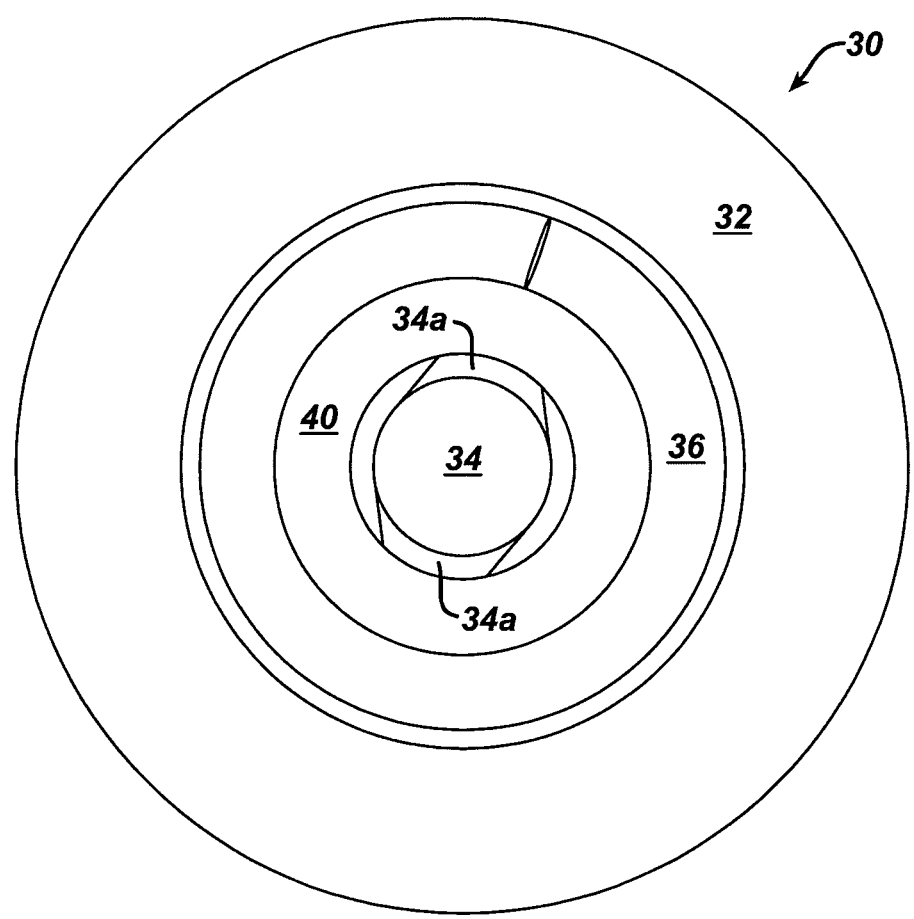
FIG. 7 is an end view of the device of FIG. 5.
Figure 10:
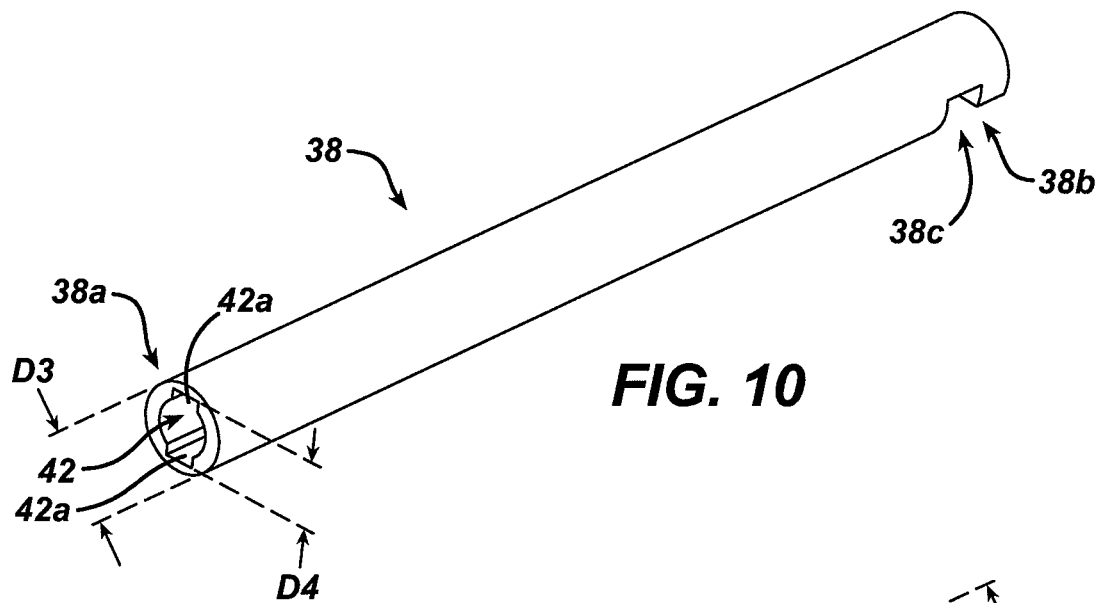
FIG. 10 is a perspective view of a suture spool of the device of FIG. 9.

The suture spool 38, shown as an independent element in FIG. 10, can also have a variety of sizes, shapes, and configurations. The suture spool 38 can be rigid, flexible, or a combination thereof, but it is preferably rigid to help keep the coil of suture 36 wrapped therearound in a substantially fixed, coiled position. As illustrated, the suture spool 38 is substantially elongate and cylindrical and has the pathway 42 extending between open distal and proximal ends 38a, 38b, but the suture spool 38 can have any shape, e.g., cone-shaped, truncated cone-shaped, rectangular, etc. The suture spool 38 can have a constant or varying shape along its longitudinal length and can have a uniform or non-uniform diameter along its longitudinal length. As best seen in FIG. 7, the suture spool's maximum outer diameter D3 is preferably sized to be disposed within the sheath's pathway 46, while the suture spool's maximum inner diameter D4 is preferably sized to allow the shaft 34 to be movably disposed within the pathway 42. The suture spool's pathway 42 can have any size and shape, but as shown, it is preferably configured to allow the shaft 34 to be movably disposed therein. Accordingly, the pathway 42 can have a substantially cylindrical core with opposed cut-outs 42a approximately 180 degrees apart around the circular core's circumference to accommodate the enlarged distal portion 34a of the shaft 34. While not necessary, the suture spool's maximum inner diameter D4 can optionally have a size and shape to allow at least a portion of the suture anchor 10 to be removably disposed within the distal end 38a of the suture spool 38. In the illustrated embodiment, however, the anchor 10 is held against the spool's distal end 38a by the shaft 34. As further discussed below, the shaft 34 can be configured to be retracted into the distal end 38a of the suture spool 38 to release the anchor 10.

The suture spool's proximal end 38b can also have various configurations, but in an exemplary embodiment it is configured to releasably couple to the spool retaining member 40. While various mating techniques can be used, in the illustrated embodiment the proximal end 38b has a cut-out 38c formed therein with a substantially half-cylinder shape having two opposed, longitudinally aligned protrusions and two opposed, longitudinally aligned depressions, although the cut-out 38c can have any configuration that can allow it to engage the spool retaining member's distal end 40a.

In an exemplary embodiment, the suture spool 38 can be non-coiled, e.g., have a smooth, non-coiled outside surface. Alternatively or in addition to a smooth outside surface, the suture spool 38 can have a plurality of grooves, a plurality of ridges, a texture, or other gripping mechanism formed on any portion of its outside surface to help hold the coil of suture 36 on its outside surface.

The coil of suture 36 can engage the suture spool 38 in any way. The coil of suture 36 is preferably disposed around the suture spool 38 in a tight coil where adjacent loops of suture are in contact to help maximize an amount of suture that can be wound around the suture spool 38. A tight coil can also help allow a larger length of suture to be delivered and made available in a body without the suture tangling en route into the body or as the coil of suture 36 is being unspooled. As shown, the coil of suture 38 can be wrapped or wound around the suture spool's outside surface. A proximal end 36b of the coil of suture 36 can be attached to the suture spool 38 to help prevent either of the coil of suture 36 or the suture spool 38 from getting misplaced or lost if released into the body. For another non-limiting example, the coil of suture 36 can be wrapped around the suture spool 38 substantially as shown but have an outer sheath disposed around the coil of suture 36 to help protect the suture from, e.g., snagging or other damage during its passage through the sheath 32 and/or introducer cannula into the body. The distal portion 36a of the coil of suture 36 can attach to the suture anchor 10 in any way, as discussed above.

The coil of suture 36 can have a variety of sizes, shapes, and configurations. Any type of suture can be used to form the coil, as discussed above. Any length of suture can be used to form the coil, generally constrained by a length of the suture spool 38 and a thickness of the suture. An uncoiled length of suture forming the suture coil can be long enough to allow the suture to extend through both ends of a scoping device inserted into a body, which can allow the suture to be cut outside the body. In an exemplary embodiment, an uncoiled length of suture forming the coil of suture 36 is at least about ten times a coiled length of the coil of suture 36, and more preferably at least about twelve times a coiled length of the coil of suture 36, e.g., about 3 feet of uncoiled suture forming about a 3 inch long coil.

Figure 11:
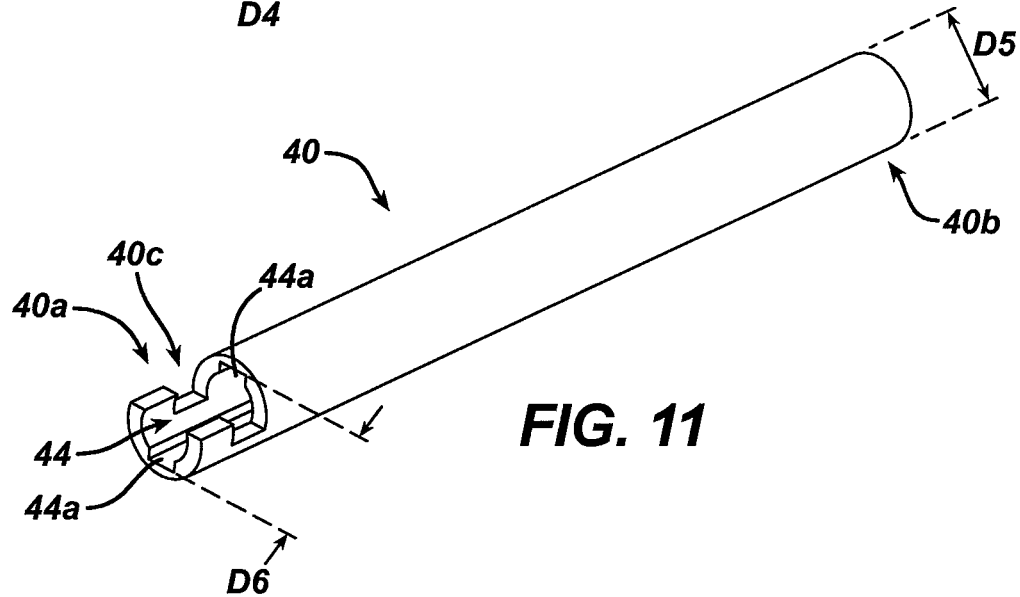
FIG. 11 is a perspective view of a suture spool retaining member of the device of FIG. 9.

The spool retaining member 40, shown as an independent element in FIG. 11, can also have a variety of sizes, shapes, and configurations. The spool retaining member 40 can be rigid, flexible, or a combination thereof, but it is preferably rigid to help effectively engage with the suture spool 38. As illustrated, the spool retaining member 40 is substantially elongate and cylindrical and has the pathway 44 extending between open distal and proximal ends 40a, 40b, but the spool retaining member 40 can have any shape, e.g., cone-shaped, truncated cone-shaped, rectangular, etc. The suture spool 38 and the spool retaining member 40 are illustrated as having the same substantially cylindrical shape, but the suture spool 38 and the spool retaining member 40 can have different shapes. The spool retaining member 40 can have a constant or varying shape along its longitudinal length and can have a uniform or non-uniform diameter along its longitudinal length. As best seen in FIG. 7, the spool retaining member's maximum outer diameter D5 is preferably substantially equal to the suture spool's maximum outer diameter D3 to also be disposed within the sheath's pathway 46, while the spool retaining member's maximum inner diameter D6 is preferably substantially equal to the suture spool's maximum inner diameter D4 to allow the shaft 34 to be movably disposed within the pathway 44. The spool retaining member's pathway 44 can have any size and shape, but as shown, it is preferably substantially the same as the suture spool's pathway 42 and configured to allow the shaft 34 to be movably disposed therein. Accordingly, the pathway 44 can have a substantially cylindrical core with opposed cut-outs 44a approximately 180 degrees apart around the circular core's circumference to accommodate the enlarged distal portion 34a of the shaft 34. In an exemplary embodiment, the cut-outs 44a in the pathway 44 of the spool retaining member 40 can extend only partially through the pathway 44, for example only in a distal portion of the pathway 44. Such a configuration can allow the distal end 34a of the shaft 34 to be fully retracted into the spool retaining member 40 yet prevent the shaft 34 from being removed out of the proximal end 40b of the spool retaining member 40, thus preventing accidental release of the spool retaining member 40 into the patient's body. Such a configuration can also allow the shaft 34 to engage and rotate the spool retaining member 40 to release the suture spool 38 therefrom, as discussed further below.

Figure 12:
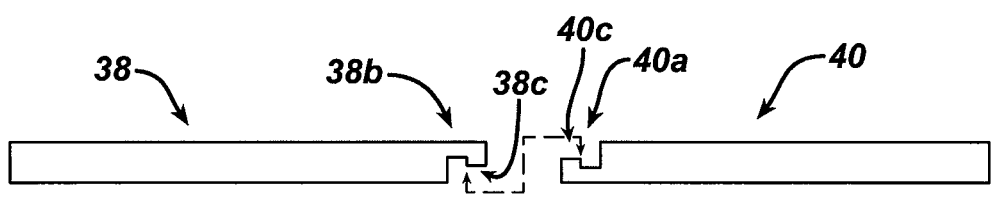
FIG. 12 is a side view of the suture spool of FIG. 10 and the suture retaining member of FIG. 11.

As indicated above, the spool retaining member's distal end 40b can be configured to releasably coupled to the proximal end 38b of the suture spool 38, and thus can include a complementary cut-out 40c formed therein. The spool retaining member's distal cut-out 40c can generally correspond to the suture spool's cut-out 38c having a half-cylinder shape with two opposed, longitudinally aligned protrusions and two opposed, longitudinally aligned depressions engageable with, respectively, the suture spool's depressions and protrusions, as best seen in FIGS. 8 and 12. When the suture spool 38 and the spool retaining member 40 are so mated together their corresponding cut-outs in the pathways 42a, 44a can substantially align to allow the shaft 34 to pass therethrough. When the shaft 34 is disposed through the spool retaining member 40 and the suture spool 38, the shaft 34, in combination with the cut-outs 38c, 40c, can prevent release of the suture spool 38 from the spool retaining member 40. When the shaft 34 is removed from the suture spool 38 and at least partially disposed in the spool retaining member 40, as discussed further below, the suture spool 38 and the spool retaining member 40 can be released from mated engagement.

As indicated above, the surgical device 30 can also include the outer tube or sheath 32 through which the shaft 34, the suture spool 38, and the spool retaining member 40 can be disposed. The sheath 32 is optional, as will be appreciated by a person skilled in the art, although use of the sheath 32 can help protect the components of the device 30 from damage, fluid, tissue debris, interference with other devices, etc. In an exemplary embodiment, the sheath 32 can be composed of at least one biocompatible and flexible material to allow the sheath 32 to be passable through a tortuous pathway and to be introduced into a body of a patient through a working channel of a flexible scoping device (or through an auxiliary channel of a flexible scoping device) having at least its distal end disposed in a body. The sheath 32 can have any size, shape, and configuration. In an exemplary embodiment, the sheath 32 can be substantially cylindrical. The sheath 32 can have a uniform or non-uniform diameter along its longitudinal length. In an exemplary embodiment, a maximum diameter D7 of the sheath 32 can be about 3.5 mm, and in some embodiments less than about 1.8 mm, which can allow the sheath 32 to be advanced through a device channel, natural orifice, body incision, etc. having a diameter greater than or equal to the diameter D7 of the sheath 32. Conventional scoping device working channels have a diameter of about 3.7 mm or about 1.8 mm, and a shaft having a maximum diameter D7 of about 3.5 mm or about 1.8 mm can easily be disposed within the working channel. The sheath 32 can have a tapered nose 48, as illustrated, having a truncated-cone shape at its distal-most end, although the nose 48 can have another tapered shape, e.g., a cone shape, or not be tapered at all. A tapered nose 48 can help the sheath 32 more easily be inserted into a scoping device and/or pass through tissue. The sheath 32 can be cannulated with the pathway 46 extending therethrough, as mentioned above, through which the anchor 10, the shaft 34, the suture spool 38 with the coil of suture 36 disposed thereon, and the spool retaining member 40 can be passed. As best seen in FIGS. 7 and 8, the sheath pathway's 46 diameter D8 is preferably greater than a maximum diameter D9 of the coil of suture 36, or whichever other element disposed through the sheath 32 has the largest maximum diameter, to allow the desired components to pass through the pathway 46.

The device 30 can also include various other features, such as a handle at its proximal end to help guide the device 30 into a body, move the shaft 34, deploy and/or unwind the coil of suture 36, and/or perform any other functions as will be appreciated by a person skilled in the art. Any type of handle having any configuration can be used. Various non-limiting embodiments of handles are described in previously mentioned U.S. Patent Publication No. 2007/0112384 and in commonly owned U.S. Patent Publication No. 2008/0103527, which is hereby incorporated by reference in its entirety.

The anchor 10 can be inserted through tissue in a variety of ways, as will be appreciated by a person skilled in the art. For non-limiting example, a needle, a knife, or other cutting element can be introduced to the body through a scoping device, through the sheath 32, and/or in any other way appreciated by a person skilled in the art. In this illustrated exemplary embodiment, the cutting tip 15 on the anchor 10 can be used to penetrate tissue.

The anchor 10 can cut tissue in any way, e.g., puncturing, slicing, etc., but as mentioned above, in an exemplary embodiment, the anchor 10 can be configured to be slidably and rotatably movable relative to the sheath 32. In this way, the anchor's cutting tip 15 can be safely contained within the sheath 32 in a retracted position when desired, thereby preventing the tip 15 from cutting any undesired tissue (or any other undesired matter). When desired, the anchor 10 can be slidably advanced through the sheath 32 to a deployed position to extend at least the cutting tip 15 beyond the sheath's distal end 32a to allow the cutting tip 15 to cut tissue. The anchor 10 can be slidably advanced through the sheath 32 by, e.g., advancing the shaft 34 which is coupled to the anchor 10 through the sheath 32.

Any or all portions of the anchor 10 can be rotatable, thereby allowing at least the cutting tip 15 to penetrate tissue and, if sufficiently rotated, causing an opening to form in the tissue. The cutting tip 15 can be rotated in a variety of ways, as will be appreciated by a person skilled in the art. In an exemplary embodiment, the anchor 10 can be configured to be rotatable relative to the tissue to be penetrated and/or the sheath 32 such that rotating the anchor 10, e.g., from a proximal end of the device 30, can also rotate the cutting tip 15. The anchor 10 can be rotated in a variety of ways, although in an exemplary embodiment, the shaft 34 can be configured to be rotatable relative to the tissue to be penetrated and/or the sheath 32 and to correspondingly rotate the anchor 10. The shaft 34 can be rotated in a variety of ways, although in an exemplary embodiment, as mentioned above, a handle and/or controls can be disposed at the shaft's proximal end 34b to help manipulate the shaft 34 and thus also the cutting tip 15, as will be appreciated by a person skilled in the art. Since the suture spool 38 can rotate with the shaft 34, and the spool retaining member 40 can be coupled to the suture spool 38, the suture spool 38 and the spool retaining member 40 can rotate with the anchor 10. Alternatively, the distal portion 34a of the shaft 34 can be moved distally beyond the distal end 38a of the suture spool 38 to allow the shaft 34 with the anchor 10 coupled thereto to rotate relative to the suture spool 38 and the spool retaining member 40.

At least a portion of the device 30, e.g., a portion of the shaft 34 engaged with the anchor 10, can be advanced through the opening formed in the tissue by the cutting tip 15. Because the device 30 can deliver the anchor 10 with the cutting tip 15 to the tissue and can thus be located proximal to the opening when it is formed by rotation of the cutting tip 15, the device 30 can be advanced through the opening soon after the opening is formed. Using rotation to penetrate tissue instead of direct application of pressure, such as when puncturing tissue with a needle, can also help reduce risk of injuring tissue on the other side of the penetrated tissue.

Figure 13:
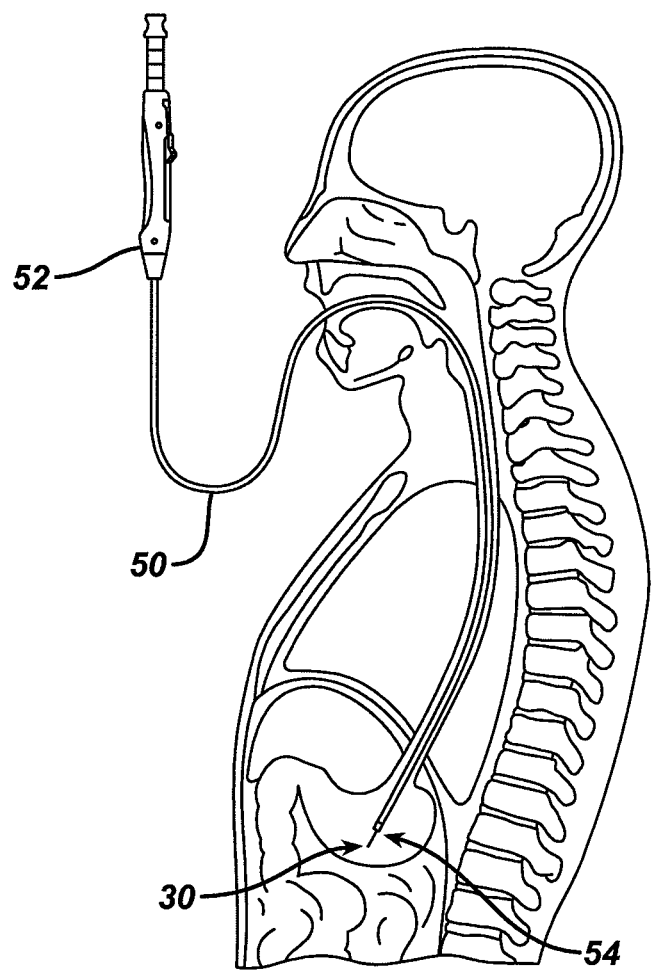
FIG. 13 is a schematic view of a flexible endoscope inserted into the upper gastrointestinal tract of a patient.

FIGS. 13-18 illustrate the device 30 in use in a minimally invasive surgical procedure to deliver and apply the anchor 10 to a tissue of a patient. FIG. 13 illustrates a flexible endoscopic portion 50 of a scoping device, e.g., an endoscope 52, inserted into the upper gastrointestinal tract of a patient with the device 30 disposed therein with the device's distal end, e.g., the sheath's distal end 32a and/or the anchor's cutting tip 15, extending beyond a distal end 54 of the endoscope 52. The device 30 is preferably delivered to a surgical site beyond the endoscope's distal end 54 through a working channel 56 of the endoscope 52 in a manner known to a person skilled in the art, e.g., by manipulating a proximal end of the shaft 34 extending outside a proximal end of the endoscope 52 after the endoscope's distal end 54 has been advanced to a desired location adjacent tissue, although the device 30 can be delivered to a surgical site in other ways and at any time during a surgical procedure. Although FIGS. 13-16 illustrate the use of the device 30 in an endoscopic procedure involving a system that includes the endoscope 52 having a working channel 56 through which the device 30 can be delivered to a surgical site, a person skilled in the art will appreciate that these and/or similar devices can be used in other ways in other types of surgical procedures. Furthermore, the tissue to which the anchor is attached can be any tissue, e.g., the stomach wall, the intestinal wall, the colon, etc.

As shown in FIG. 14, the cutting tip 15 of the anchor 10 can be positioned near a tissue 58. The anchor 10 can be moved from its retracted position inside the endoscope 52 and/or the sheath 32 to a deployed position where its cutting tip 15 is advanced beyond the endoscope's distal end 54. Any length of the device 30 can be advanced beyond the endoscope's distal end 54 in so positioning the cutting tip 15. The anchor 10, and more particularly the nose 26 including the cutting tip 15, can be positioned at any angle with respect to a contact surface 58' of the tissue 58, although in an exemplary embodiment the anchor's longitudinal axis A is substantially orthogonal to the contact surface 58' to help maximize the amount of rotational force applied to the tissue 58 upon rotation of the cutting tip 15 and to more quickly and easily penetrate the tissue 58.

FIG. 15 shows the anchor 10 in a rotation position where at least the cutting tip 15 extends beyond the endoscope's distal end 54 and is being rotated with respect to the tissue 58 to begin to pierce into the tissue 58 at a portion of the tissue 58 desired to be at least partially penetrated. The cutting tip 15 (and any other portion of the device 30 being rotated, e.g., the shaft 34) can be rotated any number of times and can rotate in a clockwise and/or a counter-clockwise direction. The rotation, in combination with the tapered shape of the anchor's nose 26 and/or with pushing the anchor 10, e.g., by pushing the shaft 34 from its proximal end, can create or increase the size of an opening in the tissue 58. At least a portion of the anchor 10 can penetrate a portion of the tissue 58.

With the opening formed at the desired location, any portion of the device 30 can be advanced through the tissue opening to effect a surgical procedure. Optionally, the opening can be maintained and/or increased by the use of other devices (not shown). The device 30 can optionally include a tissue stop, e.g., one or more protruding members located on an outside surface of the sheath 32, to help limit the penetration depth of the device 30 through the tissue 58 and to help prevent injury to tissue on the distal, "blind" side of the tissue 58 being penetrated. Various tissue stops can be used as will be appreciated by a person skilled in the art, with non-limiting examples of a tissue stop described in previously mentioned U.S. Patent Publication No. 2007/0112385.

Figure 17:
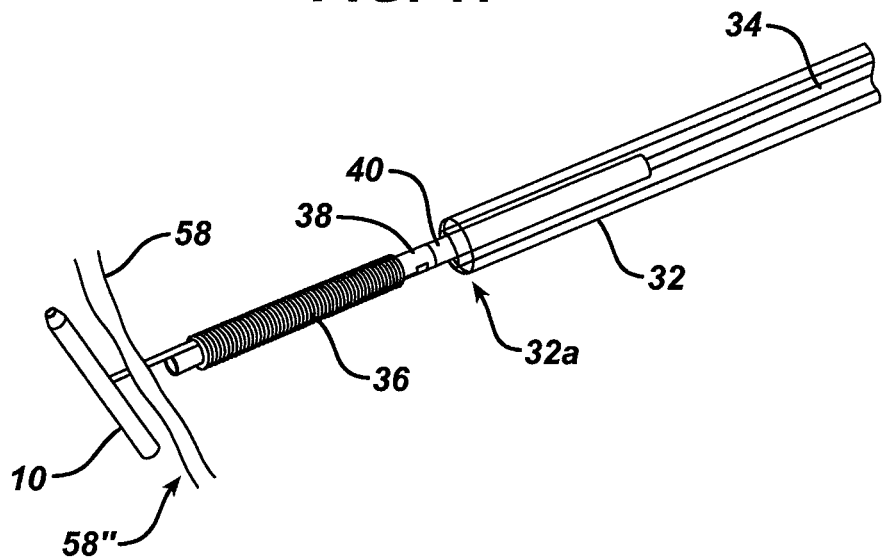
FIG. 17 is a perspective partially cross-sectional transparent view of the suture anchor and a suture spool pushed from the device of FIG. 16.

FIG. 16 shows the device 30 in an advanced position with the sheath's distal end 32a penetrated through the opening in the tissue 58 created by the anchor 10 and inside the body cavity distal to the penetrated tissue 58. Once the anchor 10 is positioned beyond the tissue wall 58, the anchor 10 can be deployed from the shaft 34. Deployment can be achieved by retracting the proximal end of the shaft 34 to proximally pull the anchor 10 against the distal end 38a of the suture spool 38. Further proximal movement of the shaft 34 can pull the distal portion 34a of the shaft 34 out of the anchor 10 and into the suture spool 38, thereby releasing the anchor 10 from the device 30. Alternatively, the anchor 10 can likewise be released by pushing the suture spool 38 and the spool retaining member 40 distally over the shaft 34 to push the anchor 10 distally off of the distal portion 34a of the shaft 34. FIG. 16 also shows the anchor 10 deployed into the body cavity distal to the penetrated tissue 58. Once the anchor 10 is advanced through the tissue, since suture is attached to a mid-portion of the elongate body of the anchor 10, a tensile force applied to the suture can cause the anchor 10 to pivot approximately 90 degrees to lie substantially parallel to a distal side 58" of the tissue 58, thereby engaging the tissue 58. FIG. 17 shows the anchor 10 deployed and rotated, e.g., with the anchor's longitudinal axis A no longer substantially axially aligned with the device's longitudinal axis L.

With the anchor 10 deployed, the suture spool 38 can remain on the opposite side of the tissue 58. The coil of suture 36 attached to the anchor 10 can unwind into the body cavity from the suture spool 38 as the anchor 10 is deployed. The coil of suture 36 can also or instead be manually unwound at any time during the surgical procedure, e.g., by using a surgical instrument such as a grasper introduced through a working channel of the endoscope 52 or in any other way appreciated by a person skilled in the art. The coil of suture 36 can also unwind if the suture spool 38 is not deployed from the device 30 before the device 30 is retracted through the endoscope's working channel 56, which can allow the coil of suture 36 to remain attached to the anchor 10 deployed in the body while unwinding from around the suture spool 38 and out the sheath's distal end 32a to extend through the working channel 56, thereby allowing the suture to be cut outside the body. Similarly, if the coil of suture 36 is deployed in the body, the coil of suture 36 can unwind in the working channel 56 when and if the coil of suture 36 still attached at its distal end to an anchor or other material in the body is removed from the body through the endoscope 52.

Figure 18:
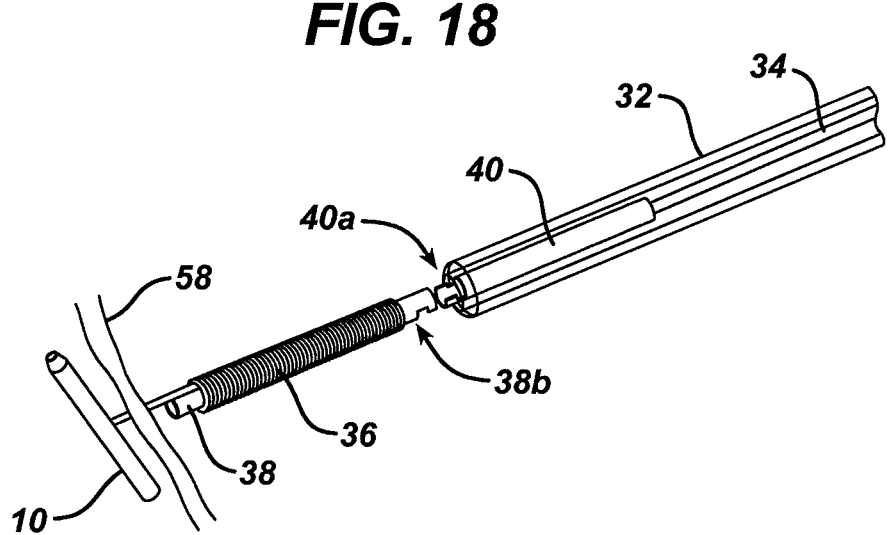
FIG. 18 is a perspective partially cross-sectional transparent view of the suture spool deployed from the device of FIG. 17.

The suture spool 38, and hence also the coil of suture 36 disposed thereon, can be optionally deployed from the device 30 at any time following the anchor's deployment. FIG. 17 shows the suture spool 38, and hence also the coil of suture 36 disposed thereon, in a pre-detached position with the suture spool 38 advanced beyond the sheath's distal end 32a. FIG. 18 shows the suture spool 38, and hence also the coil of suture 36 disposed thereon, in a detached position where the suture spool 38 and the coil of suture 36 are released from the device 30. The suture spool 38 can be detached from the device 30 in any way. In this illustrated embodiment, the shaft 34 can be retracted from the suture spool 38 through suture spool's pathway 42, with at least a portion of the shaft's distal portion 34a being disposed in the spool retaining member's pathway 46. With the shaft 34 no longer disposed in the suture spool's pathway 42, the interlocking proximal and distal ends 38b, 40a of the suture spool 38 and the spool retaining member 40, respectively, can disengage. Depending on the position of the device 30 in the body, gravity can disengage the suture spool 38 from the spool retaining member 40. Alternatively or in addition, the spool retaining member 40 can be moved relative to the sheath 32 and/or the endoscope 52 to help disengage the suture spool 38 therefrom. The spool retaining member 40 can be moved in any way and in any number of directions. In an exemplary embodiment, the shaft 34 can be rotated as discussed above, which can rotate the spool retaining member 40 because of the enlarged distal portion 34a of the shaft 34 being at least partially disposed in the spool retaining member's pathway 44. Such rotation can allow the suture spool 38 to disengage from the spool retaining member 40, e.g., after an at least 90 degree rotation of the shaft 34 and the spool retaining member 40, although the shaft 34 and the spool retaining member 40 can be rotated by any amount clockwise and/or counterclockwise. The shaft 34 can also or instead be moved laterally, shaken, wiggled, or otherwise moved to help disengage the suture spool 38 and the spool retaining member 40. Optionally, a surgical instrument, e.g., a grasper, can be used to help disengage the suture spool 38 and the spool retaining member 40.

Once released, the anchor 10 and the coil of suture 36 can be located on opposite sides of the tissue 58 such that the suture attached to the deployed anchor 10 can extend through the tissue 58 substantially at the location of the opening. The suture extending from the anchor 10 can be secured using a knotting element, e.g., a pushable knot. If multiple anchors are deployed, sutures extending from two or more of the anchors can be secured together with a knotting element. Various non-limiting embodiments of knotting elements are described in commonly owned U.S. Patent Publication No. 2007/0270889 and in PCT Patent Application No. PCT/US2008/062203 entitled "Loader for Knotting Element" which are hereby incorporated by reference in their entireties.

Any length of suture in the coil of suture 36 can be detached from the anchor 10 following the anchor's deployment in any way, e.g., using an endoscopic cutting instrument to trim suture, as will be appreciated by a person skilled in the art. This can allow any remaining length of suture in the coil of suture 36, whether it has uncoiled from the suture spool 38 or not, to be used in any way during the surgical procedure, e.g., to be unwound using a surgical instrument such as a grasper to secure tissue, to secure the deployed anchor 10 with one or more other anchors, etc., without having to remove the device 30 from the body or introduce another surgical instrument to deliver additional suture.

One or both of the device 30 and the endoscope 52 can be removed from the surgical site and the patient's body at any point following deployment of the anchor 10 and, optionally, the coil of suture 36. If the suture spool 38 is deployed into the body, it along with any unused suture in the coil of suture 36, can be removed from the body at any time during the surgical procedure in any way appreciated by a person skilled in the art, e.g., by using a surgical instrument such as a grasper.

Following the device's removal from the body, e.g., by retracting the device 30 through the endoscope's working channel 56, the device 30 can optionally be reloaded with another suture anchor to be deployed. Another suture spool with another coil of suture disposed thereon can also be reloaded into the device 30. The device 30, with any reloaded elements disposed therein, can be advanced again into the body through the endoscope 52 or in any other way, and the reloaded anchor and/or suture spool can be deployed as discussed above. Such removal, reloading, and reintroduction of the device 30 can repeat as many times as desired during a surgical procedure.

In an exemplary embodiment, a plurality of suture anchors, each having a suture attached thereto, can be deployed through tissue using the device 30 (and/or any other devices, as will be appreciated by a person skilled in the art) prior to forming a puncture in the tissue. At least one coil of suture attached to one of the deployed anchors can be released into the body for subsequent use. The puncture can be formed after deployment of a desired number of anchors and a desired number of coils of suture, and the surgical procedure can be performed as desired. At any time during the procedure, preferably at the end of the procedure, sutures attached to respective deployed anchors can be grasped and manipulated, e.g., using a grasper, to tie sutures attached to the anchors together and to close the puncture.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture anchor deployment apparatus, comprising:
a suture anchor configured to engage tissue;
a shaft coupled to the suture anchor and having a distal end configured to deploy the suture anchor from the shaft by moving proximally relative to the suture anchor; and
a suture spool releasably disposed around the shaft with the shaft movably disposed within an inner pathway extending through the suture spool, the suture spool having a suture coiled around the suture spool and coupled to the suture anchor at least in a predeployment configuration before the suture anchor is deployed from the shaft.

2. The apparatus of claim 1, wherein the suture anchor is removably coupled to a distal end of the shaft.

3. The apparatus of claim 2, wherein the distal end of the shaft is configured to be retracted into the inner pathway of the suture spool through a distal end of the suture spool to release the suture anchor.

4. The apparatus of claim 1, wherein the shaft is configured to rotate the suture anchor to cause the suture anchor to penetrate through tissue.

5. The apparatus of claim 4, wherein the suture anchor includes a circular cutting tip.

6. The apparatus of claim 1, wherein the suture anchor has a tapered distal end.

7. The apparatus of claim 1, further comprising a sheath disposed around the suture spool with the suture spool disposed within an inner pathway of the sheath.

8. The apparatus of claim 7, wherein the sheath is flexible such that the sheath can be passed through a tortuous pathway.

9. The apparatus of claim 1, further comprising a spool retaining member releasably coupled to a proximal end of the suture spool.

10. The apparatus of claim 9, wherein the shaft is disposed through the spool retaining member and is effective maintain the suture spool and the spool retaining member in mated engagement.

11. The apparatus of claim 10, wherein rotating the spool retaining member, with the shaft removed from within the inner pathway of the suture spool, is effective to release the suture spool from mated engagement with the spool retaining member.

12. The apparatus of claim 9, wherein the proximal end of the suture spool has at least one protrusion releasably coupled to a corresponding depression formed in the spool retaining member.

13. The apparatus of claim 1, wherein the suture has an uncoiled length that is at least about ten times a coiled length of the suture.

14. The apparatus of claim 1, wherein the suture is configured to remain coupled to the suture anchor after the suture anchor is deployed from the shaft.

15. The apparatus of claim 1, wherein the suture spool having the suture coiled therearound is configured to be deployed from the shaft after the distal end of the shaft deploys suture anchor.

16. A suture anchor deployment apparatus, comprising:
a suture spool having a suture wound therearound, a proximal end of the suture being directly attached to the suture spool;
a suture anchor held by a shaft against a distal end of the suture spool, a distal end of the suture being directly attached to the suture anchor; and the shaft disposed through the suture spool and configured to advance the suture anchor through tissue with the proximal end of the suture attached to the suture spool and the distal end of the suture attached to the suture anchor.

17. The apparatus of claim 16, wherein the shaft is configured to rotate the suture anchor to cause the suture anchor to penetrate through tissue.

18. The apparatus of claim 17, wherein the suture anchor has a beveled edge at its distal end configured to cut tissue.

19. The apparatus of claim 16, further comprising a spool retaining member releasably coupled to a proximal end of the suture spool and disposed around the shaft.

20. The apparatus of claim 19, wherein rotating the spool retaining member, with the shaft removed from the suture spool, is effective to release the suture spool from mated engagement with the spool retaining member.

21. The apparatus of claim 16, wherein the shaft is movably disposed through an inner pathway extending through the suture spool having the suture wound therearound, and the shaft is configured to advance the suture anchor through the tissue with the distal end of the suture attached to the suture anchor and the suture wound around the suture spool.

22. The apparatus of claim 16, wherein a proximal end of the suture anchor directly abuts the distal end of the suture spool.

* * * * *